United States Patent [19]

Das

[11] 4,211,531

[45] Jul. 8, 1980

[54] COLORIMETRIC CHOLESTEROL ASSAY

[75] Inventor: Manik L. Das, Ballwin, Mo.

[73] Assignee: Sigma Chemical Company, St. Louis, Mo.

[21] Appl. No.: 31,773

[22] Filed: Apr. 20, 1979

[51] Int. Cl.$^2$ ............... G01N 33/16; G01N 21/22; G01N 31/02
[52] U.S. Cl. ................... 23/230 B; 23/909; 252/408; 422/61
[58] Field of Search ............. 23/230 B, 909; 252/408; 422/61

[56] References Cited

U.S. PATENT DOCUMENTS

| | | | |
|---|---|---|---|
| 3,558,516 | 1/1971 | Wybenga | 23/909 X |
| 3,736,263 | 5/1973 | Parekh | 23/230 B X |
| 3,894,844 | 7/1975 | Diago | 23/230 B |
| 4,012,196 | 3/1977 | Frings | 252/408 |

OTHER PUBLICATIONS

Chemical Abstracts, 73:11265y (1970).
Chemical Abstracts, 85:119074x (1976).

*Primary Examiner*— Marantz
*Attorney, Agent, or Firm*—Polster, Polster and Lucchesi

[57] ABSTRACT

A total cholesterol method includes the steps of (1) precipitation of serum proteins with a reagent containing ferric chloride in propionic acid, (2) color formation by heating aliquots of supernatant with propionic-sulfuric acid reagent, and (3) measurement of color intensities of test and standard reaction mixtures at 563 nm.

11 Claims, No Drawings

COLORIMETRIC CHOLESTEROL ASSAY

BACKGROUND OF THE INVENTION

Numerous methods have been employed for the determination of cholesterol in biological fluids, in which a reagent combines with cholesterol in the fluid to form a colored reaction product. The concentration of cholesterol in the sample is then determined by measuring the depth or intensity of the color.

Previously known colorimetric methods for determining cholesterol have suffered from a lack of sensivity, from interference such as may be caused by hemoglobin, bilirubin, and icteric and turbid specimens, from the instability or danger of the reagents utilized, or from the length of time required for the determination. The generally recognized reference method of Abel et al, *J. Biol. Chem.* 195, 357 (1952) requires difficult and time-consuming saponification and ether extraction steps and is subject to variances caused by loss of cholesterol in the isolation process. The procedure of Jung et al, *Clinical Chemistry* 21, 1526 (1975) requires a dangerous reagent, uranyl acetate. A number of procedures have been based on the ferric chloride/sulfuric acid method of Zak, *Am. J. Clin. Pathol.* 27, 583 (1957). When sulfuric acid, acetic acid, and ferric ion are added to a sample of biological fluid, the ferric ion combines with cholesterol to form a characteristic color. Other components of the fluid, such as bilirubin, react with the reagent, however, in the well-known Hopkins-Cole reaction, to form interfering colors. Therefore, protein is first precipitated from the biological sample by the addition of ferric chloride and acetic acid. These procedures lack sensitivity and suffer from the instability of the reagents.

SUMMARY OF THE INVENTION

One of the objects of this invention is to provide a method for the determination of cholesterol which is highly sensitive and requires minimum volumes of test specimen and reagents.

Another object is to provide such a procedure which requires few manipulations and permits the determination to be made within a short period, such as ten minutes.

Another object is to provide such a procedure which avoids interference from icteric, turbid, lipemic, and hemolyzed specimens, and which avoids a glyoxylic reaction initiated by species such as serum globulins.

Another object is to provide such a procedure which employs stable, relatively safe reagents.

Another object is to provide such a method which provides accurate and reproducible results.

Other objects will become apparent to those skilled in the art in light of the following disclosure.

The present invention attains the foregoing objects by a modification of the method of Zak, supra, in which propionic acid is utilized rather than acetic acid. In the determination of total cholesterol, the method includes a first step in which serum proteins are precipitated from a serum sample by a reagent containing colorimetrice amounts of propionic acid and ferric ion. The amount of cholesterol remaining in solution is then determined by means of a reagent containing colorimetric amounts of propionic acid and sulfuric acid.

In the specification and claims, the term "colorimetric amount" means a quantity of a reagent sufficient to provide measurable and reproducible color with cholesterol in the described procedure. The term "cholesterol" when not otherwise modified, refers to cholesterol esters as well as free cholesterol.

The reagents of the invention are stable indefinitely and provide an unexpectedly sensitive cholesterol test procedure free from the effects of interfering substances.

In a preferred method, protein is precipitated from a serum sample by mixing the sample with a reagent containing ferric chloride and propionic acid. After centrifuging, the supernatant is mixed with a reagent containing propionic acid and sulfuric acid. The color-forming reaction is conveniently speeded by heating the solution for one minute in a boiling water bath, then cooling the solution before the color is measured. Preferably, a blank and a standard are run with each test specimen or group of test specimens.

Although the amounts of reagents which are "colorimetric" in the reaction will depend on the amounts of other reagents and upon the reaction conditions, preferably the protein precipitation reagent consists essentially of from about 0.5 to about 2.5 grams per liter of ferric chloride in propionic acid. The cholesterol color reagent preferably consists essentially of sulfuric acid and propionic acid, the sulfuric acid constituting from 20% to 60% of the reagent by volume. The color development step preferably includes heating the reaction mixture to a temperature of from about 50° C. to about 100° C. for a period of from about thirty seconds to about two minutes.

It will be understood that although the precipitation step and the color development step are both preferably utilized in a complete cholesterol determination, the precipitation step may be followed by other steps for determining some or all of the cholesterol in the supernatant. Likewise, the color development step may be practiced on biological fluids which may have been pretreated by other methods.

DESCRIPTION OF THE PREFERRED EMBODIMENT

The following examples are illustrative of the preferred embodiment of the present invention.

EXAMPLE I

Preparation of Reagents

A protein precipitation reagent (reagent A) is prepared by dissolving 15.0 grams of ferric chloride hexahydrate in 10 liters of propionic acid. The solution is stored at room temperature and is protected from light.

A cholesterol color reagent (reagent B) is prepared by adding slowly with stirring 4.0 liters of ice-cold concentrated sulfuric acid into 6.0 liters of ice-cold propionic acid. Care is taken that during the addition of sulfuric acid the temperature of the mixture does not increase more than 5° C. The mixture is stored at room temperature and is protected from light.

Both reagents are stable for more than a year.

EXAMPLE II

Determination of Total Cholesterol

Three leak-proof, acid-resistant, centrifuge tubes equipped with glass stopper or screw cap with Teflon liner are marked Blank, Standard and Test.

To the tube marked Blank is added 0.1 ml of water. To the tube marked Standard is added 0.1 ml of a cholesterol standard consisting of a solution of 200 milligrams of cholesterol in 100 milliliters of isopropanol. To the tube marked Test is added 0.1 ml of serum containing an unknown amount of cholesterol. To each tube is added 3.0 ml of protein precipitation reagent (reagent A). The tubes are capped. The solutions are then mixed well and centrifuged to precipitate protein.

From each tube is transferred 1.0 ml of clear supernatant to a corresponding clean, empty tube marked Blank, Standard and Test. To each tube is added 5.0 ml of cholesterol color reagent (Reagent B). The solutions are mixed well, and the tubes are heated 1 minute in a boiling water bath. The tubes are then cooled 1 minute in a cold water bath, and the solutions are again mixed well.

The absorbance of the Test and Standard solutions is read at 560 nm in a colorimeter, using the Blank solution as a reference.

The cholesterol concentration in the serum sample is determined by dividing the absorbance of the Test solution by the absorbance of the Standard solution and multiplying by the concentration of cholesterol in the Standard (200 milligrams per 100 ml).

The same procedure carried out with reagents stored for one year at room temperature shows no significant difference in results.

Under the employed conditions, the reaction color obeys Beer's Law up to 400 milligrams per 100 milliliters cholesterol concentration. Quantitative measurements of higher concentrations of cholesterol in serum samples are made by making appropriate dilutions of the sample.

The method was compared with the reference method of Abell et al, J. Biol. Chem. 195, 357 (1952) in forty-seven replicate determinations with samples containing cholesterol in concentrations of from 77 to 440 milligrams per 100 ml. Values found by the present method were found to equal 1.07 (X) −4.8, where X is the value in accordance with the method of Abell et al. The coefficient of correlation was 0.9874. The present method is believed to be more accurate and reproducible than the reference method. It is highly sensitive and permits the determination of cholesterol in samples as small as 0.05 to 0.1 ml. It avoid interference from bilirubin, hemoglobin, icteric and turbid specimens, and uses reagents that are found to be far more stable than those containing acetic acid.

Although a preferred embodiment of the invention has been described, it will be understood that many variations, within the scope of the appended claims, may be made.

I claim:

1. In a method of determining cholesterol in a biological sample comprising a precipitation step for precipitating protein in the sample, a color forming step for forming in the resulting supernatant a color proportional to the concentration of at least one form of cholesterol in the sample, and a step of determining the depth of color formed, the improvement wherein said precipitation step is carried out by means of a reagent comprising colorimetric amounts of propionic acid and ferric ion.

2. The method of claim 1 wherein said biological sample is human serum.

3. The method of claim 1 wherein said color forming step is carried out in a solution containing a colorimetric amount of sulfuric acid and propionic acid.

4. In a method of determining cholesterol in a biological sample comprising a color forming step of forming a reaction mixture including at least a fraction of said serum and a color forming reagent and thereafter a step of relating the depth of color formed to the amount of at least one form of cholesterol in said reaction mixture, the improvement wherein said reaction mixture contains a colorimetric amount of sulfuric acid and propionic acid.

5. The method of claim 4 wherein said biological sample is human serum.

6. The method of claim 5 wherein said reaction mixture further comprises a colorimetric amount of ferric ion.

7. A method of determining cholesterol in a sample of human serum, said method comprising a first step of precipitating protein in said sample by means of a protein precipitation reagent comprising colorimetric amounts of propionic acid and ferric ion, to produce a generally protein-free supernatant, a second step of developing color in a reaction mixture comprising said supernatant and a cholesterol color reagent, said cholesterol color reagent comprising colorimetric amounts of propionic acid and sulfuric acid, and a third step of relating the depth of color formed to the amount of cholesterol in said sample.

8. The method of claim 7 wherein said protein precipitation reagent consists essentially of from about 0.5 to about 2.5 grams per liter of ferric chloride dissolved in propionic acid.

9. The method of claim 8 wherein said cholesterol color reagent consists essentially of sulfuric acid and propionic acid, said sulfuric acid constituting from 20% to 60% of said cholesterol color reagent by volume.

10. The method of claim 8 wherein said second (color development) step includes heating said reaction mixture to a temperature of from about 50° C. to about 100° C. for a period of from about thirty seconds to about two minutes.

11. A reagent kit for determination of total cholesterol, said reagent kit comprising a first container containing a colorimetric amount of ferric chloride and propionic acid and a second container containing a reagent comprising colorimetric amount of propionic acid and sulfuric acid.

* * * * *